United States Patent [19]

Raines et al.

[11] Patent Number: 5,389,537
[45] Date of Patent: Feb. 14, 1995

[54] NUCLEASE HAVING ALTERED SPECIFICITY

[75] Inventors: Ronald T. Raines; Stephen B. del Cardayré, both of Madison, Wis.

[73] Assignee: Wisconsin Alumni Research Foundation, Madison, Wis.

[21] Appl. No.: 184,604

[22] Filed: Jan. 21, 1994

[51] Int. Cl.$^6$ .............................................. C12N 9/22
[52] U.S. Cl. ..................... 435/199; 435/195; 435/810
[58] Field of Search ................ 435/199, 195, 810

[56] References Cited

PUBLICATIONS

Beintema, J. J., "Structure, Properties and Molecular Evolution of Pancreatic-Type Ribonucleases," *Life Chemistry Reports*, 4:333–389 (1987).
Deutscher, M. P., "The Metabolic Role of RNases," *TIBS*, 13:136–139 (1988).
"New Products for Molecular Biology," *Boehringer Mannheim Catalog*, p. 8 (Jul. 1993).
Ribonuclease Protection Assay information pamphlet, *Ambion*, 1993.
Guardian TM RNase Protection Assay Kit, CLON-TECHniques, *Clontech*, Apr. 1993.
Meador III, J. et al., "Purification and characterization of *Escherichia coli* RNase I: Comparisons with RNase M," *Eur. J. Biochem.*, 198:549–553 (1990).
RNase One TM, *Promega Catalog*, p. 59 (1992–1993).
Raines, R. T., "Engineering to Explore and Exploit Ribonuclease A Function, " (Abstract), presented at Scientific meeting in Capri, Italy, May 11, 1993.
Ehretsmann, C. P. et al., "mRNA degradation in procaryotes," *FASEB Journal*, 6:3186–3192 (1992).
Gutti (1978) J. Biol. Chem. 263, 3837–3842.

*Primary Examiner*—Keith Baker
*Attorney, Agent, or Firm*—Quarles & Brady

[57] ABSTRACT

A ribonuclease molecule altered at a single amino acid, relative to its wild-type form, displays altered substrate specificity and substrate binding mechanism. The altered protein cleaves RNA efficiently after C, U and A residues, whereas the wild-type protein cannot cleave efficiently after A. The change that alters the specificity also permits the protein to cleave poly (A) portions of an RNA molecule processively.

5 Claims, 2 Drawing Sheets

SEQUENCE LISTING ( 1 ) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 767 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 22..396

(xi) SEQUENCE DESCRIPTION: SEQ ID NO:1:

```
GGAATTCCGC CTTCCCTGGG C AAG GAA ACT GCA GCA GCC AAG TTT GAG CGG           51
                        Lys Glu Thr Ala Ala Ala Lys Phe Glu Arg
                         1               5                  10

CAG CAC ATG GAC TCC AGC ACT TCC GCT GCC AGC AGC TCC AAC TAC TGT           99
Gln His Met Asp Ser Ser Thr Ser Ala Ala Ser Ser Ser Asn Tyr Cys
             15                  20                  25

AAC CAG ATG ATG AAG AGC CGG AAC CTG ACC AAA GAT CGA TGC AAG CCA          147
Asn Gln Met Met Lys Ser Arg Asn Leu Thr Lys Asp Arg Cys Lys Pro
         30                  35                  40

GTG AAC ACC TTT GTG CAC GAG TCC CTG GCT GAT GTC CAG GCC GTG TGC          195
Val Asn Thr Phe Val His Glu Ser Leu Ala Asp Val Gln Ala Val Cys
     45                  50                  55

TCC CAG AAA AAT GTT GCC TGC AAG AAT GGG CAG ACC AAT TGC TAC CAG          243
Ser Gln Lys Asn Val Ala Cys Lys Asn Gly Gln Thr Asn Cys Tyr Gln
 60                  65                  70

AGC TAC TCC ACC ATG AGC ATC ACC GAC TGC CGT GAG ACC GGC AGC TCC          291
Ser Tyr Ser Thr Met Ser Ile Thr Asp Cys Arg Glu Thr Gly Ser Ser
 75                  80                  85                  90

AAG TAC CCC AAC TGT GCC TAC AAG ACC ACC CAG GCG AAT AAA CAC ATC          339
Lys Tyr Pro Asn Cys Ala Tyr Lys Thr Thr Gln Ala Asn Lys His Ile
                 95                 100                 105

ATT GTG GCT TGT GAG GGA AAC CCG TAC GTG CCA GTC CAC TTT GAT GCT          387
Ile Val Ala Cys Glu Gly Asn Pro Tyr Val Pro Val His Phe Asp Ala
             110                 115                 120

TCA GTG TAGGTCTCTA CCTAAGGCCA GAGCAGCAAG ATGCACCACT TCATCACAAA           443
Ser Val
     125

GGCACCTGCC TCTCCCCTCA TGTTTCCTTG TCCTGGGGGC AATAGCTCAA GTTAGTTAGG        503

GCTCTTATCT CTGCGCACCT TACCAGAAAC ACACACACAG GATTCCCTGG CATGAAAGCA        563

ATAACTCAAG CTAGTTAAGT CTTCTATCCA ACCCACACTT GCTCCCTGG CCTGAGTCTT         623

GCCCCTGGTG GTTTGGGGGG TGAGGAGTGG GTTGTGAGGT GGGACCTGTG TTAACCAAAT        683

CACTGCTTCT TTCAATAAAC ATACTTGCAA CCACCTGAAA AAAAAAAAA AAAAAAAAA          743

GAAAAAAAAA AAAAAAGGAA TTCC                                               767
```

(2) INFORMATION FOR SEQ ID NO:2:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:2:

```
Lys Glu Thr Ala Ala Ala Lys Phe Glu Arg Gln His Met Asp Ser Ser
 1               5                  10                  15
```

|     |     |     |     |     |     |     |     |     |     |     |     |     |     |     |     |
|-----|-----|-----|-----|-----|-----|-----|-----|-----|-----|-----|-----|-----|-----|-----|-----|
| Thr | Ser | Ala | Ala<br>20 | Ser | Ser | Ser | Asn | Tyr<br>25 | Cys | Asn | Gln | Met | Met<br>30 | Lys | Ser |
| Arg | Asn | Leu<br>35 | Thr | Lys | Asp | Arg | Cys<br>40 | Lys | Pro | Val | Asn | Thr<br>45 | Phe | Val | His |
| Glu | Ser<br>50 | Leu | Ala | Asp | Val | Gln<br>55 | Ala | Val | Cys | Ser | Gln<br>60 | Lys | Asn | Val | Ala |
| Cys<br>65 | Lys | Asn | Gly | Gln | Thr<br>70 | Asn | Cys | Tyr | Gln | Ser<br>75 | Tyr | Ser | Thr | Met | Ser<br>80 |
| Ile | Thr | Asp | Cys | Arg<br>85 | Glu | Thr | Gly | Ser | Ser<br>90 | Lys | Tyr | Pro | Asn | Cys<br>95 | Ala |
| Tyr | Lys | Thr | Thr<br>100 | Gln | Ala | Asn | Lys | His<br>105 | Ile | Ile | Val | Ala | Cys<br>110 | Glu | Gly |
| Asn | Pro | Tyr<br>115 | Val | Pro | Val | His | Phe<br>120 | Asp | Ala | Ser | Val |     |     |     |     |

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

CCAAGGAAAC TGCAGCAGCC                                                      20

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:4:

GGCCTTAGGT CGACTACTAC ACTGAAGC                                      28

NUCLEASE HAVING ALTERED SPECIFICITY

STATEMENT REGARDING FEDERALLY SPONSORED RESEARCH

This invention was made with United States Government Support awarded by the National Institute of Health (NIH), Grant No. GM44783. The United States Government has certain rights in this invention.

FIELD OF THE INVENTION

The present invention relates to the field of nuclease enzymes that cleave single-stranded nucleic acids and more particularly to modified nucleases having altered specificities. Most particularly, the invention relates to RNase A enzymes having altered specificities.

BACKGROUND OF THE INVENTION

For molecular biologists, degradation of nucleic acids using nucleases is particularly important, and is widely used in analytical and preparative methods. In particular, ribonucleases (RNases) are used to degrade ribonucleic acid (RNA) in DNA purification and RNA protection assays. RNase-mediated cleavage of the RNA sugar-phosphate backbone is by transphosphorylation followed by hydrolysis of the 2',3'-cyclic phosphate intermediate formed. The specificity with which an RNase cleaves an RNA molecule is determined by the linear arrangement, or sequence, of purines (adenine, guanine, and, rarely, inosine) and pyrimidines (cytosine and uracil) in the RNA molecule. Virtually all of the well-characterized pancreatic RNase A molecules catalyze an endonucleolytic cleavage after the 3' phosphate group of pyrimidine residues, yet cannot cleave after purine residues. However, since there is little, if any, predictability to the sequences of RNA molecules, a ribonuclease may degrade pyrimidine-rich portions of an RNA to single ribonucleotides, yet leave relatively long pieces of the molecule intact and undergraded. Undergraded oligomers are undesirable by-products in a reaction mixture since they may be long enough to contaminate subsequent reactions by, for example, hybridizing to nucleic acids of interest. It would be desirable, therefore, to provide an RNase that retains its catalytic ability but which also has an ability to catalyze cleavage reactions after residues other than pyrimidines. Such an RNase would be useful for degrading RNA polymers into smaller pieces than are now possible.

Bovine pancreatic ribonuclease A (RNase A; E.C.3.1.27.5) has been an exemplar for studies in all aspects of protein chemistry and enzymology. Because bovine pancreatic RNase A is abundant and relatively easily obtained in purified form, it is considered to be an RNase of choice for use in biotechnology. RNase A is a relatively small protein (14 kDa) that catalyzes the cleavage of the P—O$_5$, bond of RNA specifically on the 3'-side of pyrimidine nucleosides, by a two step mechanism in which a cyclic phosphate intermediate is formed. Other RNase A's that have been analyzed are quite similar in sequence and specificity to the bovine pancreatic form.

It has been inferred from structural analysis of RNase A that the sidechain of the threonine residue at position 45 (Thr45) mediates the pyrimidine specificity by forming hydrogen bonds with a pyrimidine base (U or C), and by sterically excluding the purine bases (A, G, or I). The structural data also show that the aromatic sidechain of the phenylalanine at position 120 (Phe120) stacks with the base of pyrimidine residues.

RNase A forms a three dimensional structure having at least three subsites (B1, B2, B3) that each bind to a base in polymeric RNA. Thr45 and Phe120 contribute to the B1 subsite, which is highly specific for pyrimidine bases as discussed above. Subsite B2 binds to the base 3' to the pyrimidine base in B1 and subsite B3 binds to the base 3' to the base in B2. While subsites B2 and B3 are able to accept all bases, B2 has a 100-fold preference for adenine and B3 has a 10-fold preference for adenine.

In addition to a desire to broaden the number of bases at which RNase A can cleave RNA, it would also be desirable to provide a processive RNase A that could repeatedly catalyze cleavages along the length of a single RNA polymer until every possible cleavage of the polymer has occurred. Wild-type RNase A, in contrast, is a distributive enzyme, in that after binding to an RNA polymer, the RNase A molecule catalyzes a single cleavage reaction then dissociates from the cleaved polymer. Thus, each cleavage requires a separate interaction between enzyme and substrate. A naturally occurring processive RNase is RNase II, a cytosolic enzyme from *E. coli.*

To facilitate more complete degradation of undesired RNA, molecular biologists overcome the pyrimidine specificity of pancreatic RNases by mixing a pancreatic RNase such as RNase A with RNase T1, which cleaves RNA after G residues, to form a cocktail that cleaves RNA at three of the four residues. Yet, even this approach does not ensure complete degradation of every RNA species in a reaction vessel, since phosphodiester bonds after A residues are still not cleaved.

Other solutions to the problem of incomplete RNA digestion exist. A 27 kDa periplasmic enzyme, recently cloned from *E. coli* and overproduced, cleaves the phosphodiester bond between all four nucleotide residues. Meador, J. et al., 187 *Eur. J. Biochem.* 549 (1990). However, apparently this enzyme is relatively unstable and therefore difficult to handle without rendering it inactive.

SUMMARY OF THE INVENTION

The present invention is summarized in that the specificity of a ribonuclease that can cleave a single-stranded RNA molecule may be altered by a single amino acid substitution. Like wild-type pancreatic ribonucleases, the mutant nuclease cleaves RNA chains after the pyrimidine bases uracil and cytosine. Notably, however, it also cleaves after the purine base adenine and retains the stability of wild-type RNase A.

The present invention is also summarized in that the altered ribonuclease can cleave processively rather than distributively.

It is an object of the present invention to alter the specificity and manner with which nuclease enzymes bind to and cleave RNA.

It is a feature of the present invention that a single amino acid substitution in a wild-type RNase protein is sufficient to alter the cleavage specificity and processivity of the RNase protein such that the protein cleaves after C, U, or A residues.

It is an advantage of the present invention that the mutant RNase digests RNA more completely than does wild-type RNase.

It is another advantage of the present invention that the mutant RNase A enzyme is as stable as the wild-type enzyme.

It is a further advantage of the present invention that, in combination with RNase T1, the mutant enzyme may be used to formulate an enzymatic cocktail having cleavage activity against all four RNA ribonucleotides.

Other objects, advantages and features of the present invention will become apparent upon consideration of the following detailed description read in light of the accompanying drawings.

DETAILED DESCRIPTION OF THE PREFERRED EMBODIMENT

Figure 1:
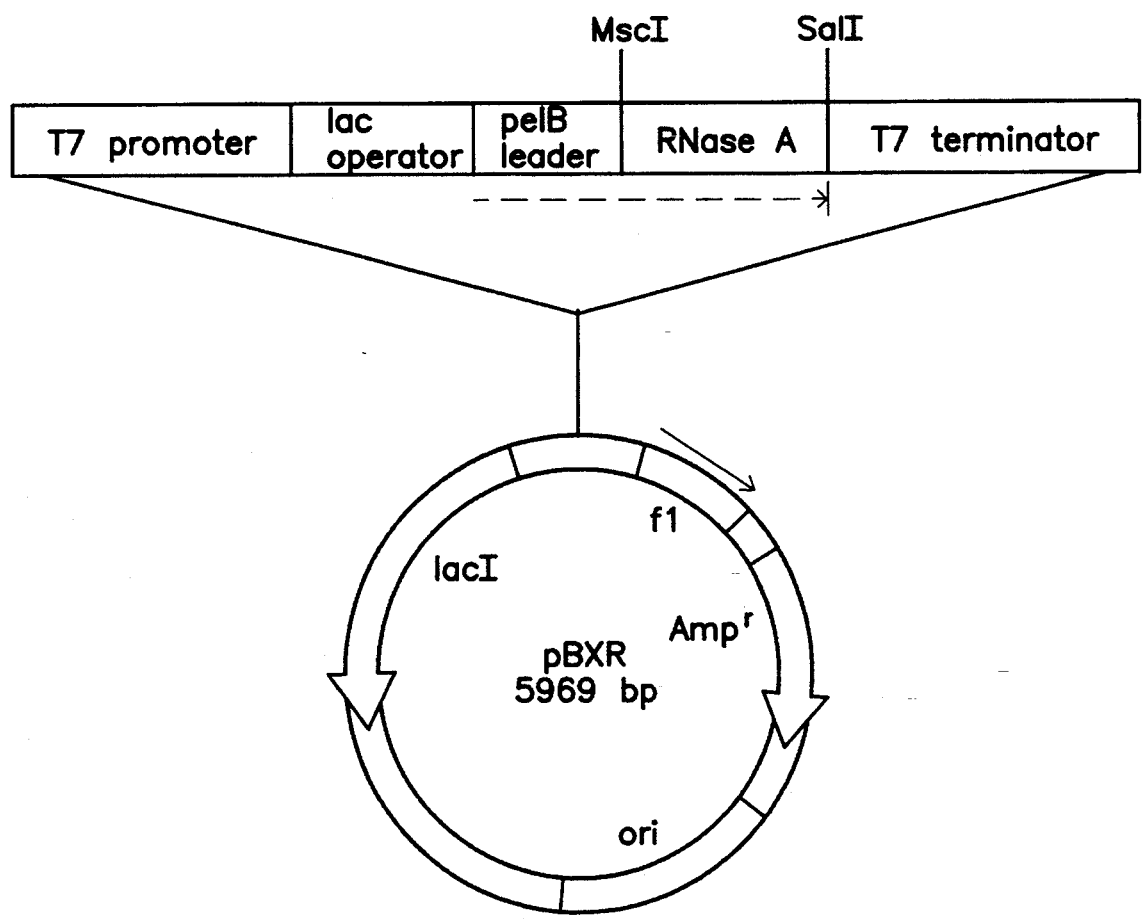
FIG. 1 is a map of plasmid pBXR.

In this patent application, a pancreatic-type ribonuclease (RNase) is any endonucleolytic RNA cleavage enzyme that yields 3'-phosphomono- and 3'-phosphooligonucleotides after transphosphorylation of RNA and hydrolysis of a cyclic intermediate. Pancreatic-type RNases are typically found in the pancreases of mammals and of a few reptiles, although related RNases from non-pancreatic sources are also known. The pancreatic-type RNases are typified by bovine pancreatic RNase A, which has been extensively studied. Unless otherwise noted, an "RNase" is a pancreatic-type RNase including bovine RNase A and other RNases related in structure and function.

The ribonucleotide bases that join together by phosphodiester linkage to form RNA molecules are adenosine (hereinafter, A), guanine (G), cytosine (C), uracil (U) and, rarely, inosine (I). In this application, a reference to one of the ribonucleotide bases is intended to signify the ribonucleotide base plus any associated phosphate or sugar groups joined thereto.

In keeping with the present invention, a nuclease enzyme having the ability to cleave a single-stranded nucleic acid molecule after pyrimidines, and after the purine A, may be obtained by altering a single amino acid in the binding site of the single chain enzyme. In most, if not all, pancreatic-type RNase molecules for which protein sequence is available, the preferred amino acid is threonine which is typically found at or near position 45. Pancreatic-type RNases are well conserved evolutionarily. It is believed that this amino acid is involved in determining the cleavage specificity of these enzymes. The specificity of pancreatic-type RNases is such that cleavage occurs only after C or U. The crystalline structure of wild-type RNase A suggests that hydrogen bonds form between the threonine at position 45 and either a C or U residue of an RNA molecule. Fersht, A. *Enzyme Structure and Mechanism*, p. 428–431, Freeman:New York (1985).

Amino acid numbers referred to in this application are counted from the first amino acid of the wild-type RNase A coding region, rather than from an engineered protein encoded by an expression vector. The first amino acid of the wild-type coding region of bovine pancreatic RNase A is lysine, which is amino acid number 1 in SEQ ID NO: 2 below.

It has been found by the present inventors that mutants at position 45 of RNase A permit cleavage after C, U, or A, thereby allowing RNase A to cleave at more sites in a typical RNA population, that is on average composed of 25% A, 25% G, 25% C, and 25% U. It is believed that other amino acids comparable to RNase A position 45 that are involved in nucleic acid binding and cleavage in other nucleases may be altered in a manner analogous to that described herein to achieve comparable changes in substrate specificity or processivity. In particular, the inventors have found that when the threonine at position 45 is replaced by glycine or alanine, the desired changes in substrate specificity are realized.

A parameter useful for quantifying the change in substrate specificity of nuclease activity is the specificity constant kcat/Km, which describes the affinity of an enzyme for the rate-limiting transition state in catalysis. It has been found here that substitutions of smaller amino acids for the threonine residue at position 45 results in a dramatic increase in specificity constant of engineered RNase A for A substrate (i.e. three to four orders of magnitude) with little loss in specificity for C or U. For effective use, all that is required is that the specificity constant for A be in the same order of magnitude, or within two orders of magnitude, as the comparable constants for C and U. It is readily possible to create engineered RNase A enzymes which have such altered specificity constants.

It has further been found that mutant RNases within the scope of the present invention cleave RNA in a more efficient manner than wild-type RNases. Whereas wild-type RNases prefer to cleave a pyrimidine in subsite B1, followed in subsites B2 and B3 by two A's, the mutant enzymes disclosed herein can cleave a pyrimidine or an A in B1 followed by two A's. Accordingly, the mutant enzyme can cut RNA processively in certain portions of the RNA, whereas the wild-type enzyme would detach from the RNA after each cleavage and bind again before the next cleavage.

To determine whether a ribonuclease cleaves a polymeric substrate processively, the chemical state of the phosphoryl group during the cleavage may be monitored. The chemical states of the phosphoryl group (i.e., acyclic diester→cyclic diester→monoester) can be distinguished by $^{31}P$ NMR spectroscopy. Further, the relative molecular weights (strand length) of each of the cleavage species can be inferred from the $^{31}P$ NMR peak shifts within a certain species, since low molecular weight species have a greater downfield shift than do high molecular weight species. For example, if the acyclic diester phosphoryl groups of poly (A) were being cleaved processively, then the spectra would show little accumulation of high molecular weight polymer containing a 3'-terminal 2'-3' cyclic diester (oligo>p). Instead, the high molecular weight polymer would be converted completely to a monomeric cyclic diester (A>p). In the case of poly (C), which is not degraded processively, however, a sizable accumulation of the oligo>p form would be expected.

It is also possible to measure the extent to which a ribonuclease bound to a substrate is temporarily prevented from binding to another substrate molecule. This prevention, referred to as distraction, is measured by allowing the enzyme to bind to a substrate and then adding additional substrate that can be distinguished from the first substrate pool. If the enzyme is processive, it would be expected that pre-incubation with unlabeled poly (A) would inhibit degradation of the later-added substrate.

Accordingly, the following distraction experiment may be performed. Unlabeled polynucleotides may be incubated in a reaction buffer with ribonuclease for a period of time, t', sufficient to allow any processive complex to form. Then, labelled (e.g., radiolabelled) polynucleotide is added to the mixture, which is incubated for additional time, t, before being quenched with a stop solution (e.g., 95% v/v formamide, 0.05% w/v xylene cyanol). In a control experiment, the labeled and unlabeled polynucleotides are mixed together and then exposed to the ribonuclease for time t. In the control, the labelled polynucleotide will be degraded without distraction, even if the enzyme can bind processively to it.

The reaction products of both experiments may be separated and visualized. It is preferred that the separation be by electrophoresis (e.g., on a 7.5% w/v acrylamide gel in 1×TBE buffer) and the visualization be by autoradiography. When processive binding exists on a substrate, the labelled substrate will not be degraded when it is added second, though it will be degraded in the control.

To obtain RNase A mutants at Thr45, the nucleotide triplet that encodes Thr45 is modified and reinserted into an expression vector that encodes an otherwise wild-type RNase A molecule. A sufficient number of different expression vectors modified at position 45 are created so that the pool of modified vectors encodes a set of RNase A proteins in which each of the 19 other natural amino acids are represented at amino acid position 45.

A suitable expression vector would encode a coding region encoding a nuclease gene under the control of appropriate control sequences that would permit transcription and translation of the gene in a desired procaryotic or eucaryotic host cell.

The coding region may be any nucleic acid that encodes a nuclease enzyme in which one or more of the enzyme's amino acids affects the enzyme's substrate specificity or processivity. Methods for determining which amino acids have such effects include examining the enzyme's predicted three dimensional structure and analyzing the intermediate adduct products of cleavage in which the RNA remains bound to particular amino acids. The coding region nucleic acid may derive from any source that is known to the art including, for example, genomic DNA, cloned fragments of genomic DNA, cDNA, or synthetic DNA fragments.

The control sequences would preferably include an upstream promoter active in the host, such as the T7 polymerase promoter in *E. coli*, and could include a termination sequence downstream of the gene. In addition, the vector can be provided with other nucleic acid sequences known to enhance transcription or translation. A selectable marker gene such as an antibiotic resistance gene for growth of the vector in a host under selective conditions may also be provided on the vector. The art is cognizant of many such marker genes and of growth conditions that permit survival only of host cells that express particular marker genes. It would also be possible to express a modified nuclease in an in vitro coupled transcription/translation system.

Because the present inventors have now demonstrated that the specificity and processivity of RNase A may be altered by providing an alanine or glycine at position 45, it is now possible to produce a modified RNase A expression vector using conventional strategies known in the molecular biological arts, without the need to resort to screening a randomly generated set of mutants. Such modified vectors could be produced, for example, by synthesizing double-stranded oligonucleotide fragments for insertion into an expression vector at the appropriate codon of the coding region. It is believed that any of the triplets that encode alanine or glycine (GCT, GCC, GCA, GCG, GGT, GGC, GGA, or GGG) could be incorporated into such a fragment at position 45.

It is noted that while this invention is primarily described in terms of mutations at Thr45 of RNase A, it is not intended to be so limited. Rather the method disclosed herein may be adapted to obtain mutants of any single-stranded nuclease at the amino acid responsible for binding the nucleotides to be cleaved.

Mutants made and isolated according to the present invention are advantageously used in a ribonuclease protection assay. Diagnostically, RNases are used in RNase Protection Assays (RPA) to destroy single-stranded RNA that has not been protected by hybridization to an RNA probe. Briefly, in an RPA, a radiolabelled RNA probe is mixed with a test RNA population, such as total cellular RNA from an individual, under conditions where complementary segments of the RNA probe and the test RNA will hybridize. RNase is then added to the mixture to destroy unprotected (unhybridized), single-stranded probe and test RNA. When all single-stranded RNA has been destroyed, only short fragments of protected RNA remain that can be analyzed electrophoretically to diagnose genetic lesions in the test RNA. The protected double-stranded RNA fragments are denatured before analysis, to make available the detectable, labeled single-stranded RNA probe fragment. In the presence of residual RNase, the labelled single-stranded RNA probe would itself be destroyed, undermining the utility of the diagnostic technique.

The invention is further clarified by consideration of the following examples, which are intended to be purely exemplary of the method of the present invention.

EXAMPLES

Plasmids

The expression vector pBXR includes a coding region derived from a cDNA molecule that encodes a wild-type bovine pancreatic RNase A. The cDNA sequence of the wild-type coding region was published in Carsana, A. et al., *Nucl. Acids Res.* 16:5491–5502 (1988) and is shown at SEQ ID NO: 1. A fragment carrying the RNase A cDNA was generated from a clone containing the RNase A gene using PCR and the 5'- and 3'- priming oligonucleotides SD3 (CCAAGGAAACTGCAGCAGCC, SEQ ID NO:3) and SD4 (GGCCTTAGGTCGACTACTACACTGAAGC, SEQ ID NO:4), respectively. The amplified fragment was band purified, treated with T4 DNA polymerase to remove any overhanging bases left by taq polymerase, and digested with SalI. The resulting fragment had the RNase A cDNA flanked on its 5' end by two CG base pairs (which form a blunt end) and on its 3' end by a SalI sticky end. This fragment was then ligated to the band-purified MscI/SalI fragment of the *E. coli* expression plasmid pET22B(+) (Novagen, Madison, Wis.), using T4 DNA ligase. The resultant vector was pBXR. RNase A gene expression in pBXR was under control of the widely available T7 promoter. Mature RNase A was directed to the periplasm by the pelB leader peptide. The first codon of mature RNase A is a lysine encoded by the nucleotides 23–25 of SEQ ID NO: 1.

The nucleotides upstream of the initial lysine encode the C-terminal portion of the pelB leader peptide. As is shown in FIG. 1, pBXR also includes a lac operator sequence and the lacI gene, along with a gene conferring ampicillin resistance.

To facilitate the mutagenesis step, a unique and translationally silent NheI (GCTAGC) site was introduced into the pBXR vector by oligonucleotide-mediated site-directed mutagenesis in two codons 3' to the Thr45 triplet. Specifically, the NheI site was created by changing the wild-type codon at Ser50 from TCC to TCG and the wild-type Leu51 from CTG to CTA. Creation of this site provided the plasmid thus formed, pBXR1, with a unique ClaI/NheI fragment that contained the Thr45 triplet. The pBXR1 expression vector has been expressed in *E. coli* and the active enzyme encoded by the vector has been purified to homogeneity in high yield.

The unique ClaI/NheI fragment was subjected to cassette-mediated saturation mutagenesis, as has been described by Reidhard-Olson, J. F. et al., *Methods in Enzymology*, 208:564–586 (1991). At codon 45, 32 mutant triplets of the form N-N-G/C were formed. At position 3 of the mutated triplets, only G and C were permitted, but all four bases were available at positions 1 and 2. The products of this mutagenesis procedure were a library of pBXR1-derivative plasmids, denoted pBXR(Thr45All), in which at least one codon for each of the 20 natural amino acids was represented at codon 45. This unsorted pool of distinct plasmids encoding mutant RNase A molecules was transformed into *E. coli* strain BL21(DE3) cells which carry an inducible gene for T7 RNA polymerase.

Purine-cleavage activity

BL21(DE3) cells carrying the pBXR(Thr45All) plasmids were induced to express the ribonuclease cDNAs by adding IPTG. After a period of growth, cells were separated from the culture medium by centrifugation and the culture medium was assayed by zymogram electrophoresis for an ability to cleave polypurine substrates (poly (A), poly (G), or poly (I)), which activity is lacking in wild-type RNase A. (see Blank, A. et al., *Anal. Biochem*, 120:267–275 (1982), Stockman, B. J. and J. L. Markley, *Adv. Biophys. Chem.*, 1:1–46 (1990), Ribo, M. et al., in *Structure, Mechanism and Function of Ribonucleases*, de Llorens, R. et al., eds., Universitat Autonoma de Barcelona, Bellaterra, Spain, 157–162 (1991), and Kim, J. S. and R. T. Raines, *Protein Sci.* 2:348–356 (1993)).

Briefly, culture media samples were diluted with SDS-PAGE loading buffer lacking any reducing agent, boiled, and separated by SDS-PAGE in a gel co-polymerized with a polypurine at 0.5 mg/ml. After electrophoresis, proteins in the gel were renatured by washing the gel twice for 10 minutes each time with 10 mM Tris-HCl buffer, pH 7.5, containing isopropanol (20% v/v) to extract the SDS, and then twice for 20 minutes each time with 10 mM Tris-HCl buffer, pH 7.5. The gel was stained for five minutes with 10 mM Tris-HCl buffer, pH 7.5 containing toluidine blue (0.2% w/v) which binds to high molecular weight nucleic acid. The gel was then destained with water. Regions in the gel that contained ribonuclease activity appear as clear bands on a blue background.

Cleavage activity against poly (A), but not against poly (G) nor poly I, was detected in the protein extracts.

To identify the active mutant plasmid or plasmids from the pool of mutants, a zymogram spot assay was performed. Briefly, 100 individual 2 ml cultures, each expressing one of the mutated pBXR(Thr45All) plasmids, were grown and induced to express their plasmid. Cells were separated from the culture medium by centrifugation and 1 microliter samples of the medium were placed on an agarose gel (1% w/v) containing poly (A) at 0.3 mg/ml and 10 mM Tris-HCl buffer, pH 7.5. The gel was then incubated at 37 degrees Centigrade for 30 minutes before being stained as described above. Once again, activity against a polypurine substrate was observed as a clear spot on a blue background.

Plasmids from two codon 45 mutants that scored positive for poly (A) cleavage were isolated and their nucleotide sequence was determined. In one of the mutants, Thr45 was substituted by alanine (T45A), encoded by GCC or by GCG. In the second, glycine, encoded by GGC or by GGG, was found at position 45 (T45G). Mutant RNase A enzymes were also purified from these plasmids' bacterial hosts using standard protein purification methods.

Substrate Specificity of T45G and T45A

Figure 2:
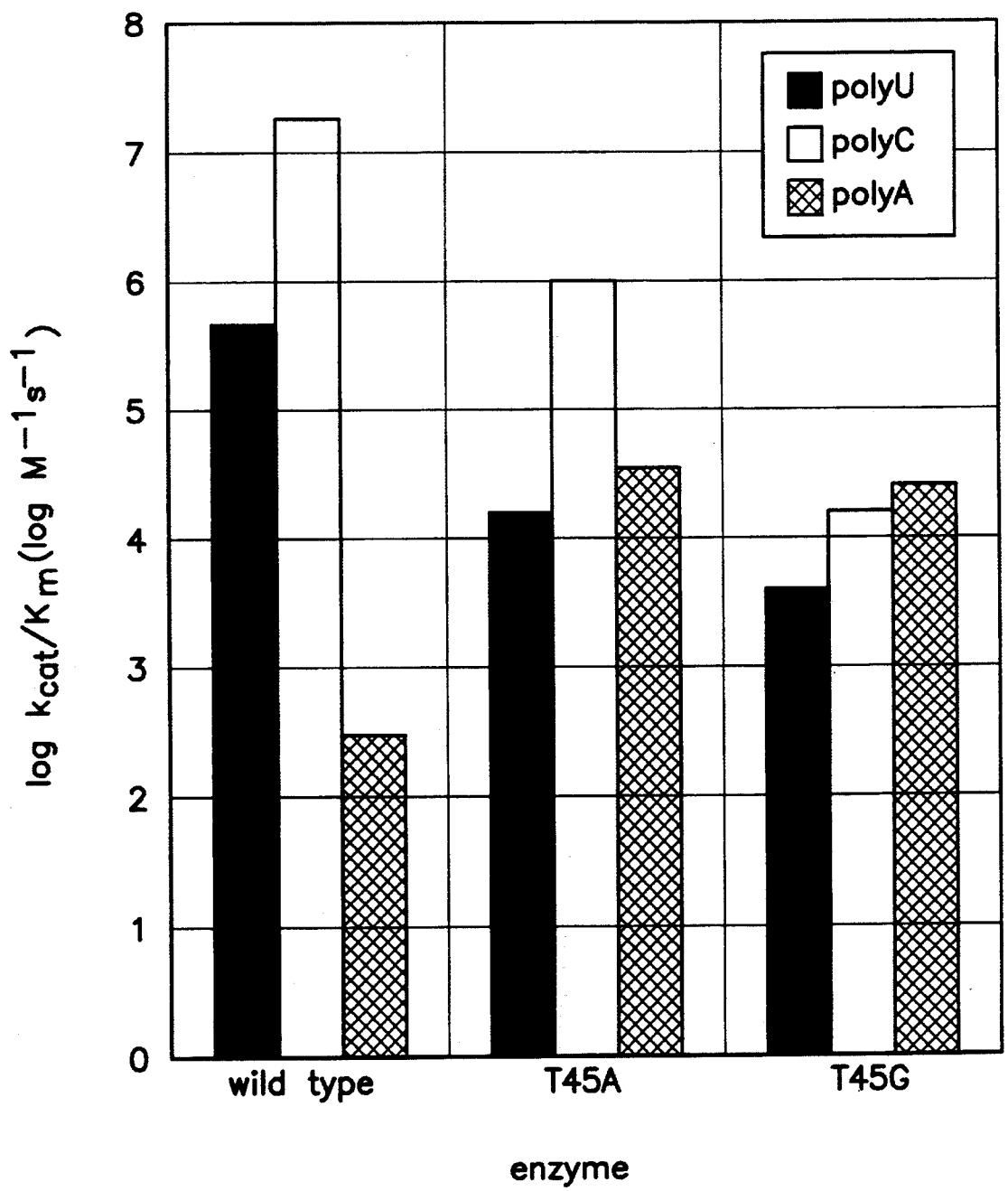
FIG. 2 depicts the relative activity on various substrates of wild-type RNase A and two mutant RNase A proteins.

To determine the efficiency with which T45G and T45A RNase A cleave poly (A), the steady-state kinetic parameters for the cleavage of the synthetic substrate UpA and the homopolymers poly (A), poly (C), and poly (U) were compared to each other and to wild-type RNase A, and are presented in FIG. 2 and in Table 1. All assays were performed at 25° C. in 0.1 MES buffer, pH 6.0, containing NaCl (0.1M), substrate (10–750 µM), and enzyme (1.0 nM–1.0 µM). Initial velocities were determined by uv spectroscopy, and were converted to M/s using measured extinction coefficients. The cleavage of UpA by RNase A and the mutants was determined using an adenosine deaminase coupled assay. The $\Delta\epsilon$ was $-6000$ $M^{-1}cm^{-1}$ for this reaction. The cleavage of poly (C), poly (U), and poly (A) were monitored by the change in hyperchromicity. The $\Delta\epsilon$ for these reactions, calculated from the difference in molar absorptivity of the polymeric substrate and the mononucleotide cyclic phosphate product, were 2380 $M^{-1}cm^{-1}$, 1360 $M^{-1}cm^{-1}$, and 6400 $M^{-1}cm^{-1}$ for poly (C) at 250 nm, poly (U) at 278 nm, and poly (A) at 260 nm. The values for $k_{cat}$, $K_m$, and $k_{cat}/K_m$ were determined by weighted non-linear least squares fit of the initial velocity data to the Michaelis-Menten equation with the program HYPERO.

TABLE 1

| RNase A | $k_{cat}$ [$S^{-1}$] | | | | $K_m$ [mM] | | | |
|---|---|---|---|---|---|---|---|---|
| | UpA | polyU | polyC | polyA | UpA | polyU | polyC | polyA |
| wild type | 1400 ± 130 | 24 ± 15 | 510 ± 10 | 0.023 ± 0.001 | 0.62 ± 0.09 | 0.06 ± 0.12 | 0.034 ± 0.001 | 0.080 ± 0.009 |
| T45A | 24 ± 13 | 1.7 ± 0.2 | 500 ± 60 | 1.4 ± 0.1 | 4 ± 2 | 0.12 ± 0.04 | 0.48 ± 0.08 | 0.041 ± 0.005 |
| T45G | 20 ± 10 | 0.86 ± 0.08 | 1000 ± 300 | 5.8 ± 0.2 | 6 ± 4 | 0.19 ± 0.04 | 4 ± 2 | 0.023 ± 0.004 |

| | $k_{cat}/K_m$ [$10^6 M^{-1}s^{-1}$] | | | |
|---|---|---|---|---|
| RNase A | UpA | polyU | polyC | polyA |

TABLE 1-continued

| | | | | |
|---|---|---|---|---|
| wild type | 2.3 ± 0.4 | 0.40 ± 0.26 | 15 ± 9 | 0.00028 ± 0.00004 |
| T45A | 0.06 ± 0.05 | 0.014 ± 0.005 | 1.0 ± 0.2 | 0.035 ± 0.005 |
| T45G | 0.0030 ± 0.0025 | 0.004 ± 0.001 | 0.2 ± 0.1 | 0.25 ± 0.04 |

| RNase A | $(k_{cat}/K_m)$polyA $(k_{cat}/K_m)$polyU | $(k_{cat}/K_m)$polyA $(k_{cat}/K_m)$polyU rel | $(k_{cat}/K_m)$polyA $(k_{cat}/K_m)$polyC | $(k_{cat}/K_m)$polyA $(k_{cat}/K_m)$polyC rel |
|---|---|---|---|---|
| wild type | $(7.0 ± 4.7) \times 10^{-4}$ | 1 | $(2 ± 1) \times 10^{-5}$ | 1 |
| T45A | 2.5 ± 1.0 | $(4 ± 3) \times 10^3$ | 0.035 ± 0.009 | $(2 ± 1) \times 10^3$ |
| T45G | 62 ± 19 | $(9 ± 7) \times 10^4$ | 1.2 ± 0.6 | $(6 ± 4) \times 10^4$ |

As the size of the amino acid residue at position 45 decreases, the value of $k_{cat}/K_m$ for poly (A) cleavage increases. This increase is a result of both an increase in $k_{cat}$ and a decrease in $K_m$. Interestingly, the $K_m$ but not the $k_{cat}$ for cleavage of poly (C) is affected by these mutations, increasing 100-fold from that of the wild-type enzyme.

The T45G mutant actually cleaves poly (A) more efficiently than it does poly (U) or poly (C). When change in substrate specificity relative to wild-type is compared:

$$(k_{cat}/K_m)_{poly\ A}/(k_{cat}/K_m)_{poly\ U} = 62(9 \times 10^4 - \text{fold change})$$

$$(k_{cat}/K_m)_{poly\ A}/(k_{cat}/K_m)_{poly\ C} = 1.2(6 \times 10^4 - \text{fold change})$$

The T45A mutant exhibited a 20- to 30- fold smaller change in substrate specificity relative to wild-type than did the T45G mutant:

$$(k_{cat}/K_m)_{poly\ A}/(k_{cat}/K_m)_{poly\ U} = 2.5(4 \times 10^3 - \text{fold change})$$

$$(k_{cat}/K_m)_{poly\ A}/(k_{cat}/K_m)_{poly\ C} = 0.035(2 \times 10^3 - \text{fold change})$$

Although both mutants cleave polymeric substrates efficiently, both have a diminished ability to bind and turnover UpA. This diminution is likely due to the loss of a large fraction of the binding interactions with this small substrate.

Processivity of T45G and T45A

The mutant RNase A's were also tested for processivity in cleaving polymeric substrates. As previously noted, wild-type RNase A is distributive and must, therefore, engage the substrate de novo for each cleavage reaction.

High molecular weight poly (C) and poly (A) were prepared by ethanol precipitation of commercial materials. Reactions were performed in 0.1M MES/0.1M NaCl buffer containing poly (C) or poly (A) at 2 mg/ml with sufficient ribonuclease to degrade the polymer completely in about 50 minutes.

Spectra were recorded in 10 mm NMR tubes having D2O inserts. Free induction decays were obtained at 25° C. on a Bruker AM400 spectrophotometer by using the following parameters: spectral width, 4854 Hz; pulse width, 18.1 μs; acquisition time, 1.69 s; relaxation delay, 3.2 s; number of scans, 64. The free induction decays were subjected to Fourier transformation with a line broadening of 5 Hz, and the resulting spectra were phased with the program FELIX (Hare Research, Bothell, Wash.). Chemical shift values were recorded relative to aqueous $H_3PO_4$ (100 mM).

During the degradation of poly (C) using either the T45A or T45G RNase A, the resonance from the acyclic diester shifted downfield from −1.30 ppm to −0.90 ppm. This shift is characteristic of a decrease in the strand length of the acyclic diester. Concurrent with this shift was the appearance of resonances for two cyclic diesters: one at 19.7 ppm (for oligo C>p) and another at 20.1 ppm (for C>p). In contrast, during the degradation of poly (A), the resonance from the acyclic diester remained at −1.03 ppm, and a single cyclic diester resonance appeared at 19.9 ppm (for A>p). The designation >p represents a 2′,3′- cyclic phosphate group in the reaction product. These data indicate that cleavage of poly (A) by T45A and T45G RNase A produces only monomeric adenyl 2′,3′- cyclic monophosphates diesters (A>p) but not polymers containing a cyclic diester (oligo A>p). This is the behavior expected from a processive nuclease.

In addition to the $^{31}P$ NMR assays, distraction assays using wild-type, T45A, or T45G RNase A, were performed as described above, on poly (A) (purine) or poly (C) (pyrimidine) substrates of about 70 nucleotides each in length. The reactions contained enzyme:labeled substrate:unlabeled substrate in a ratio of 1:10:10. The products of quenched reactions were separated on a denaturing polyacrylamide gel (7.5% w/v).

No degradation of labeled poly (A) or poly (C) was observed after pre-incubation of either mutant enzyme with unlabeled poly (A). Unlabeled poly (C), however, was unable to distract the mutant or wild-type enzymes from degrading labeled poly (C). Wild-type enzyme was not distracted by pre-incubation with either poly (A) or poly (C), since it is not processive.

These results support the idea that the T45A and T45G mutant RNase A's bind to the poly (A) substrate in a manner different from wild-type RNase A, and degrade poly (A) processively, as indicated by their distraction by, and slow release from, individual strands of poly (A). It is also apparent that the processivity does not extend to poly (C) substrates.

Taken together, the preceding examples demonstrate the creation of a nuclease that has been altered in both substrate specificity and processivity (binding mechanism), with little compromise to catalytic efficacy.

It is to be understood that the present invention is not limited to the particular embodiments disclosed in this application, but embraces all such modified forms thereof as come within the scope of the following claims.

We claim:

1. A mutant pancreatic-type ribonuclease A, the mutant differing from the wild-type ribonuclease A at amino acid position 45 and being able to cleave an RNA molecule after an A ribonucleotide.

2. A mutant of wild-type pancreatic-type ribonuclease A, the mutant having an alanine at amino acid position 45 and being able to cleave an RNA molecule after an A ribonucleotide.

3. A mutant of wild-type pancreatic-type ribonuclease A, the mutant having a glycine at amino acid position 45 and being able to cleave an RNA molecule after ribonucleotide A.

4. A kit, comprising:
a substantially purified preparation of RNase T1; and
a substantially purified preparation of a mutant of wild-type pancreatic-type ribonuclease A, the mutant having an alanine at amino acid position 45 and being able to cleave an RNA molecule after ribonucleotide A.

5. A kit, comprising:
a substantially purified preparation of RNase T1; and
a substantially purified preparation of a mutant of wild-type pancreatic-type ribonuclease A, the mutant having an glycine at amino acid position 45 and being able to cleave an RNA molecule after ribonucleotide A.

* * * * *